United States Patent
Colla et al.

(10) Patent No.: US 7,040,317 B2
(45) Date of Patent: May 9, 2006

(54) FAULT DIAGNOSIS IN CPAP AND NIPPV DEVICES

(75) Inventors: Gregory A. Colla, McMahons Point (AU); Barton J. Kenyon, Leichhardt (AU)

(73) Assignee: ResMed Limited, North Ryde (AU)

( * ) Notice: Subject to any disclaimer, the term of this patent is extended or adjusted under 35 U.S.C. 154(b) by 45 days.

(21) Appl. No.: 10/785,193

(22) Filed: Feb. 25, 2004

(65) Prior Publication Data

US 2004/0226561 A1 Nov. 18, 2004

Related U.S. Application Data

(60) Division of application No. 10/408,568, filed on Apr. 8, 2003, now Pat. No. 6,745,768, which is a continuation of application No. 09/719,680, filed as application No. PCT/AU99/00972 on Nov. 5, 1999, now Pat. No. 6,591,834.

(30) Foreign Application Priority Data

Nov. 5, 1998 (AU) .................................. PP6933

(51) Int. Cl.
*A61M 16/00* (2006.01)
(52) U.S. Cl. ............................. 128/204.18; 128/204.21
(58) Field of Classification Search ........... 128/200.24, 128/204.18, 204.21, 204.23, 204.29, 205.11, 128/205.23, 204.26; 600/529, 532, 533, 600/538
See application file for complete search history.

(56) References Cited

U.S. PATENT DOCUMENTS

| | | |
|---|---|---|
| 4,765,325 A | 8/1988 | Crutchfield |
| 4,846,166 A | 7/1989 | Willeke |
| 5,065,756 A | 11/1991 | Rapoport |
| 5,107,831 A | 4/1992 | Halpern et al. |
| 5,148,802 A | 9/1992 | Sanders et al. |
| 5,289,819 A | 3/1994 | Kroger et al. |
| 5,313,937 A | 5/1994 | Zdrojkowski |
| 5,458,137 A | 10/1995 | Axe et al. |
| 5,529,056 A | 6/1996 | Brunson et al. |
| 5,535,738 A | 7/1996 | Estes et al. |
| 5,535,739 A | 7/1996 | Rapoport et al. |
| 5,540,219 A | 7/1996 | Mechlenburg et al. |
| 5,546,789 A | 8/1996 | Balke et al. |
| 5,558,086 A | 9/1996 | Smith et al. |
| 5,603,316 A | 2/1997 | Coufal et al. |
| 5,617,849 A | 4/1997 | Springett et al. |

(Continued)

FOREIGN PATENT DOCUMENTS

EP 483 566 5/1992

(Continued)

OTHER PUBLICATIONS

U.S. Appl. No. 10/035,199, filed Jan. 2002, Brewer et al.

*Primary Examiner*—Teena Mitchell
(74) *Attorney, Agent, or Firm*—Nixon & Vanderhye P.C.

(57) ABSTRACT

A ventilation device for non-invasive positive pressure ventilation (NIPPV) or continuous positive airway pressure (CPAP) treatment of a patient has a gas flow generator, a gas delivery circuit optionally including a humidifier, a controller and sensors monitoring values of operational parameters of the device. The device further includes one or more relationships stored in data storage of the controller relating combinations of parameter values as being indicative of fault conditions of the device operation, the sensors and/or the fault detection process.

22 Claims, 18 Drawing Sheets

CPAP apparatus

U.S. PATENT DOCUMENTS

| | | | |
|---|---|---|---|
| 5,632,269 A | 5/1997 | Zdrojkowski |
| 5,647,351 A | 7/1997 | Weismann et al. |
| 5,662,099 A | 9/1997 | Tobia et al. |
| 5,685,296 A | 11/1997 | Zdrojkowski et al. |
| 5,803,065 A | 9/1998 | Zdrojkowski et al. |
| 5,823,187 A | 10/1998 | Estes et al. |
| 5,860,418 A | 1/1999 | Lundberg |
| 5,868,133 A | 2/1999 | DeVries et al. |
| 5,881,717 A | 3/1999 | Isaza |
| 5,901,704 A | 5/1999 | Estes et al. |
| 5,904,141 A | 5/1999 | Estes et al. |
| 5,937,855 A | 8/1999 | Zdrojkowski et al. |
| 5,970,975 A | 10/1999 | Estes et al. |
| 6,024,087 A | 2/2000 | Kersey et al. |
| 6,029,664 A | 2/2000 | Zdrojkowski et al. |
| 6,164,276 A | 12/2000 | Bathe et al. |
| 6,220,244 B1 | 4/2001 | McLaughlin |
| 6,253,765 B1 | 7/2001 | Hognelid et al. |
| 6,279,574 B1 | 8/2001 | Richardson et al. |
| 6,299,581 B1 | 10/2001 | Rapoport et al. |
| 6,360,741 B1 | 3/2002 | Truschel |
| 6,363,270 B1 | 3/2002 | Colla et al. |
| 6,369,838 B1 | 4/2002 | Wallace et al. |
| 6,397,841 B1 | 6/2002 | Kenyon et al. |
| 6,425,395 B1 | 7/2002 | Brewer et al. |
| 6,539,940 B1 | 4/2003 | Zdrojkowski et al. |
| 6,584,973 B1 | 7/2003 | Biondi et al. |
| 6,591,834 B1 | 7/2003 | Colla et al. |
| 6,770,037 B1 * | 8/2004 | Sullivan et al. ............ 600/529 |

FOREIGN PATENT DOCUMENTS

| | | |
|---|---|---|
| EP | 0621056 A1 | 10/1994 |
| EP | 0656216 A2 | 6/1995 |
| GB | 2281513 | 3/1995 |
| WO | WO 87/02898 | 5/1987 |
| WO | WO 96/03174 | 2/1996 |
| WO | WO 96/11717 | 4/1996 |
| WO | WO 97/28838 | 8/1997 |
| WO | WO 98/41268 | 9/1998 |

* cited by examiner

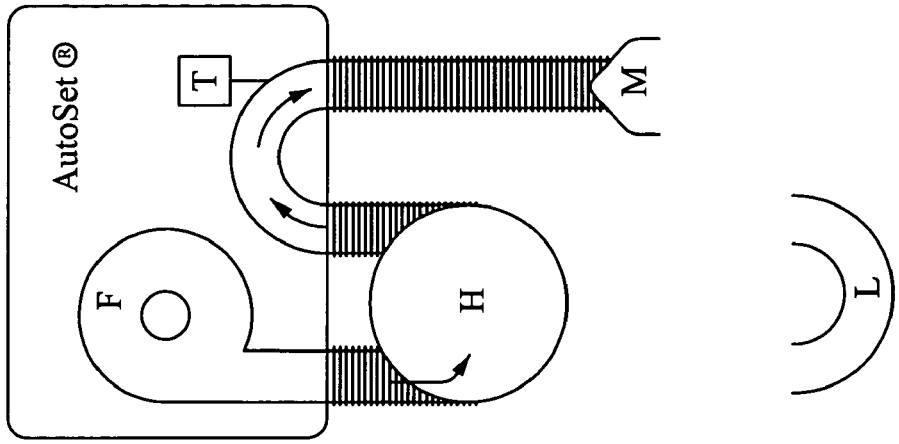
Figure 1b: *Correct attachment of tubing*
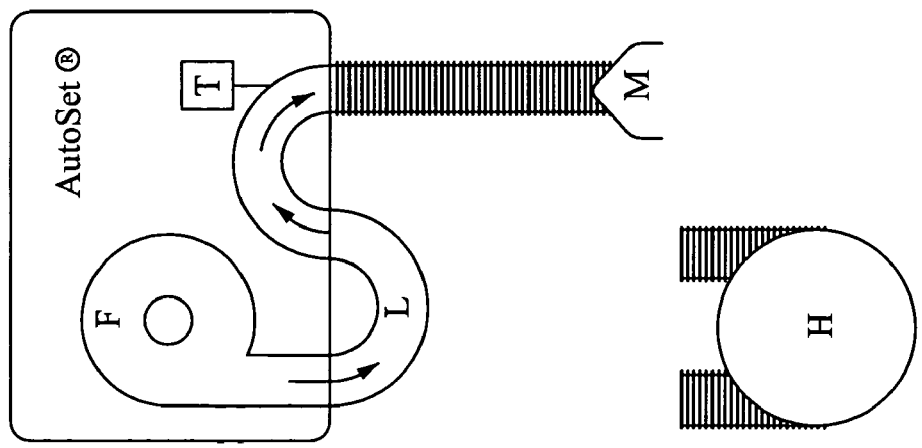
Figure 1a: *Correct attachment of tubing*

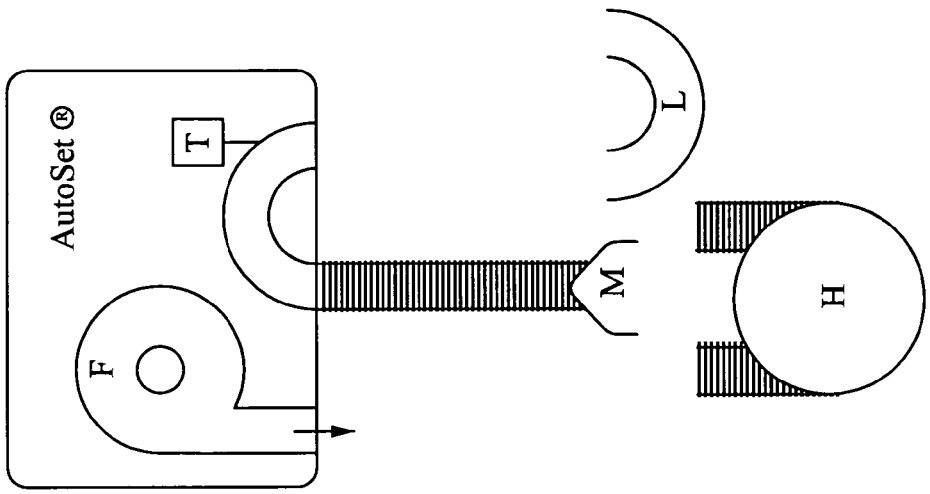
Figure 1c: *Incorrect attachment of tubing*
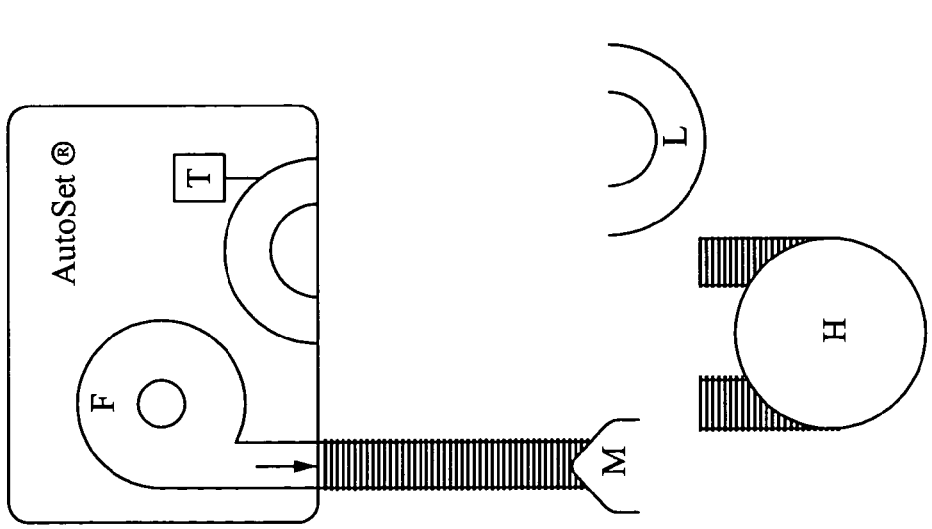
Figure 1d: *Incorrect attachment of tubing*

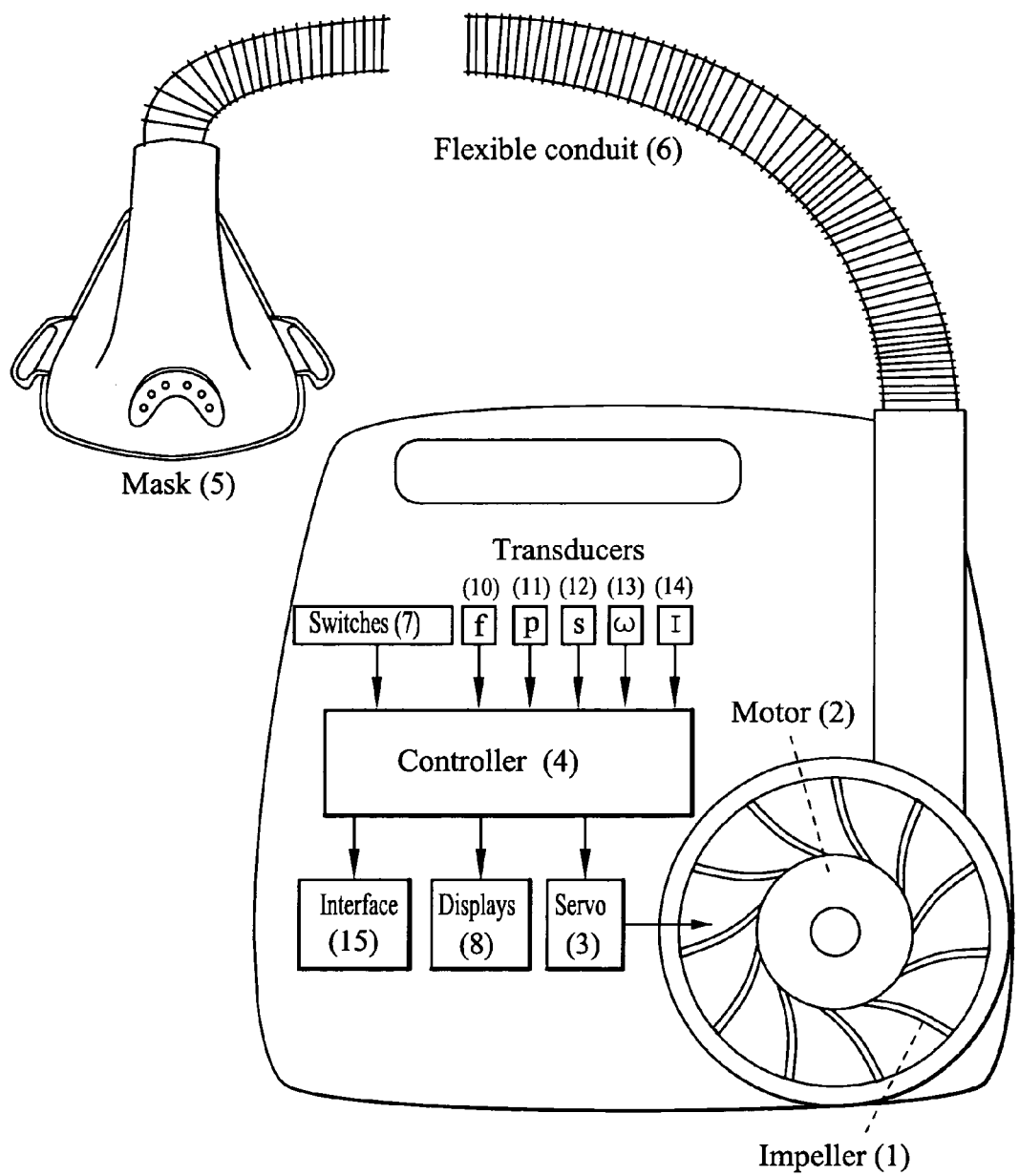
Figure 2: *CPAP apparatus*

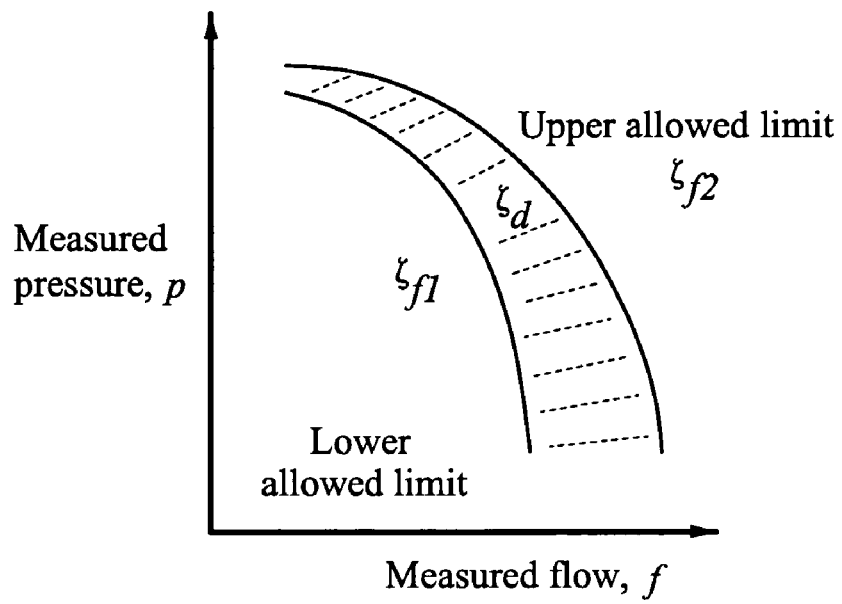
Figure 3a: *High motor speed (ω) operation*
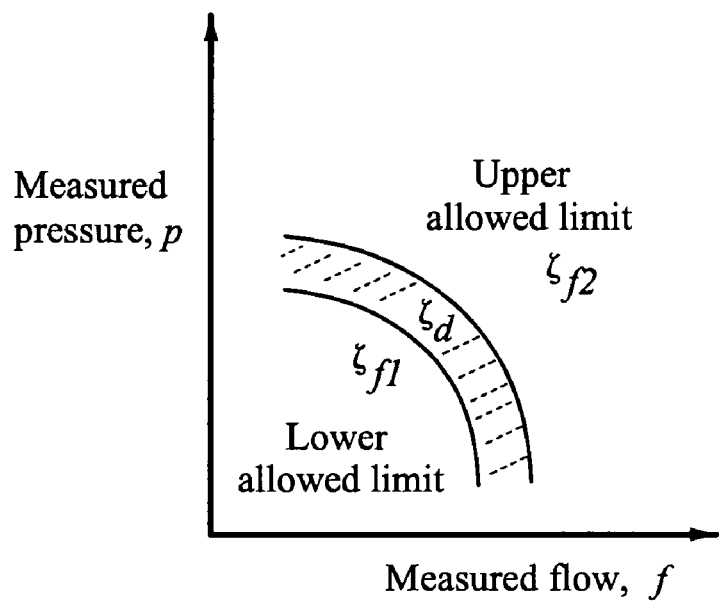
Figure 3b: *Low motor speed (ω) operation*

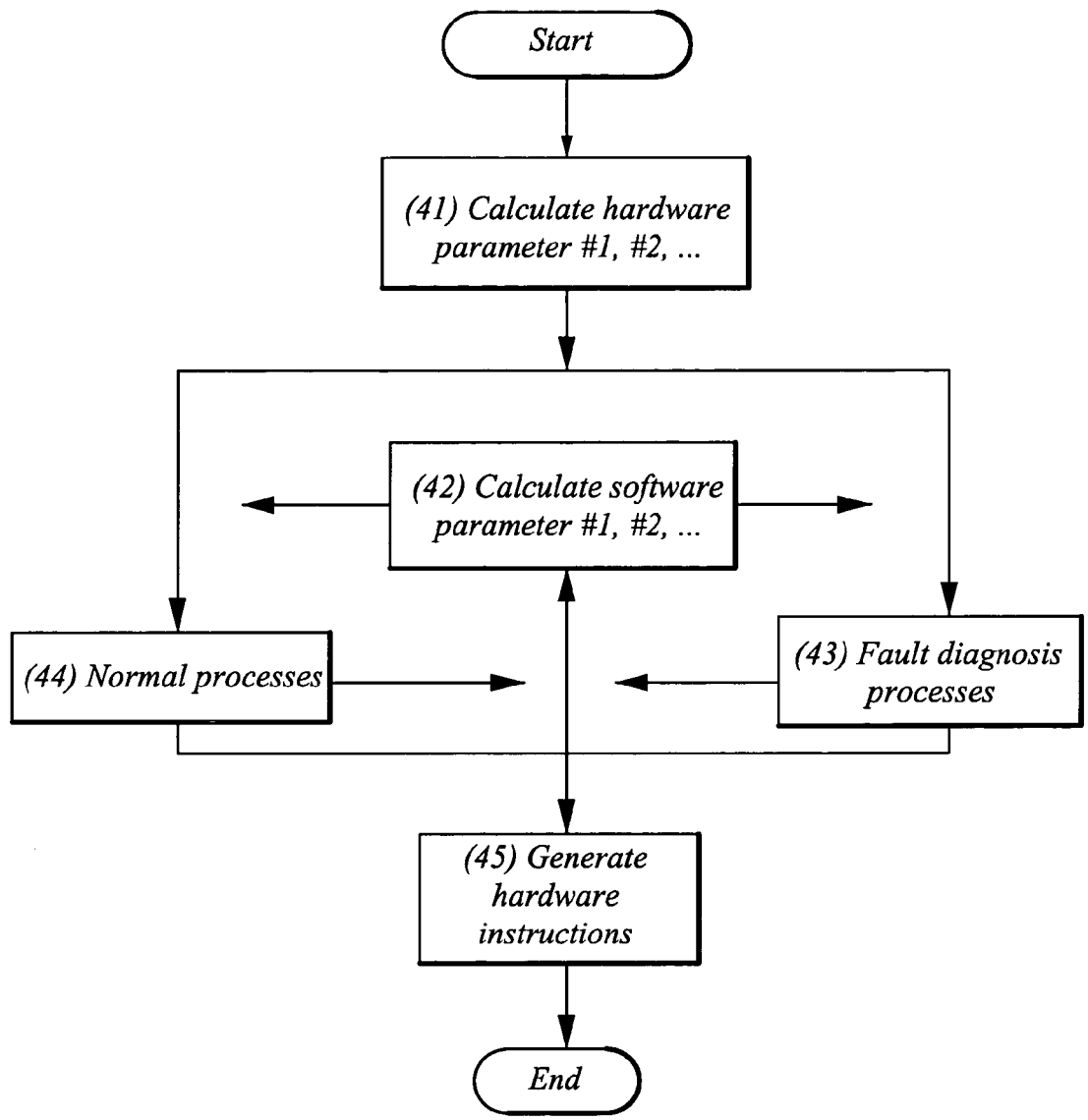
Figure 4: *Fault diagnosis implemented in overall software processes*

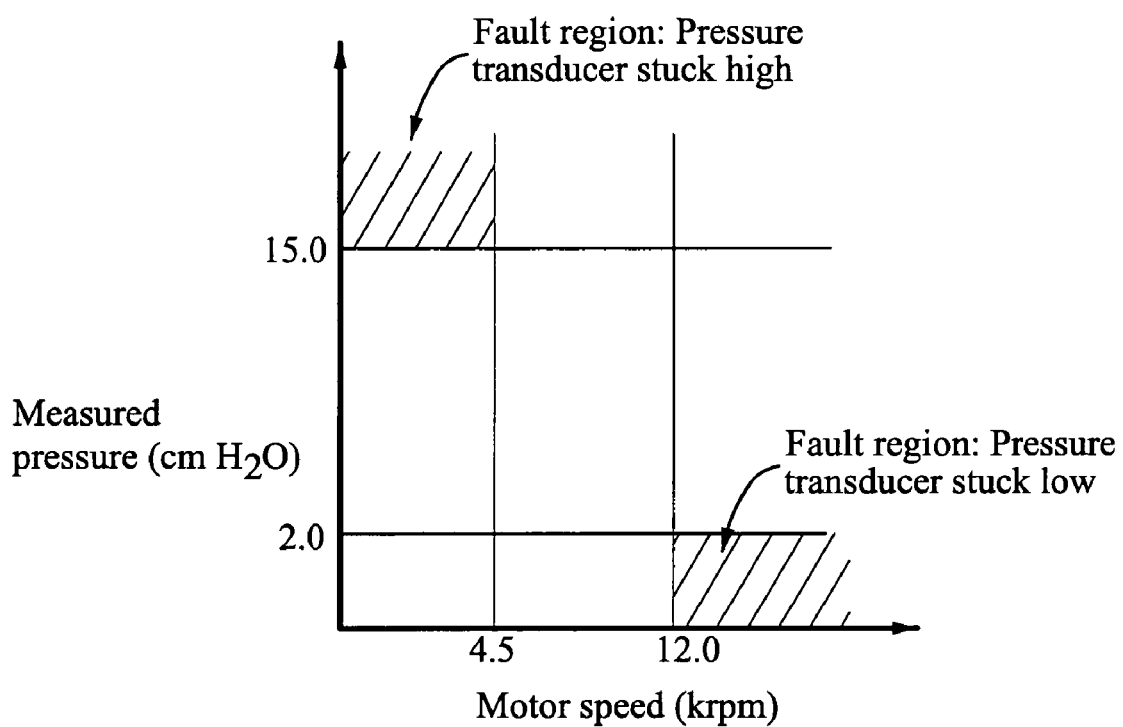
Figure 5: *Pressure transducer fault regions*

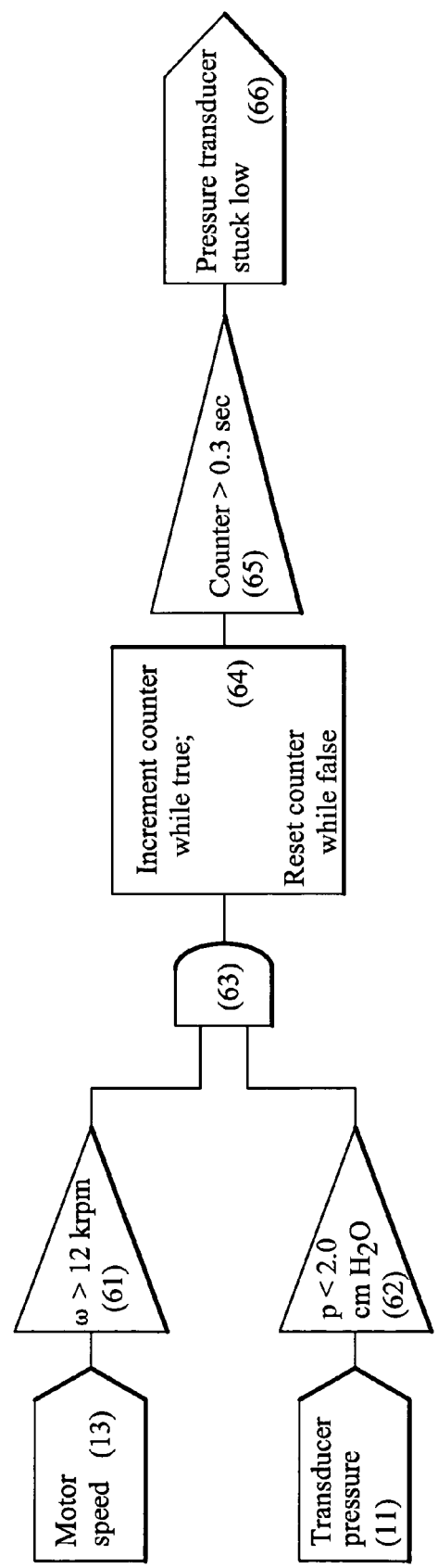
Figure 6: *Detect Pressure Transducer Stuck Low*

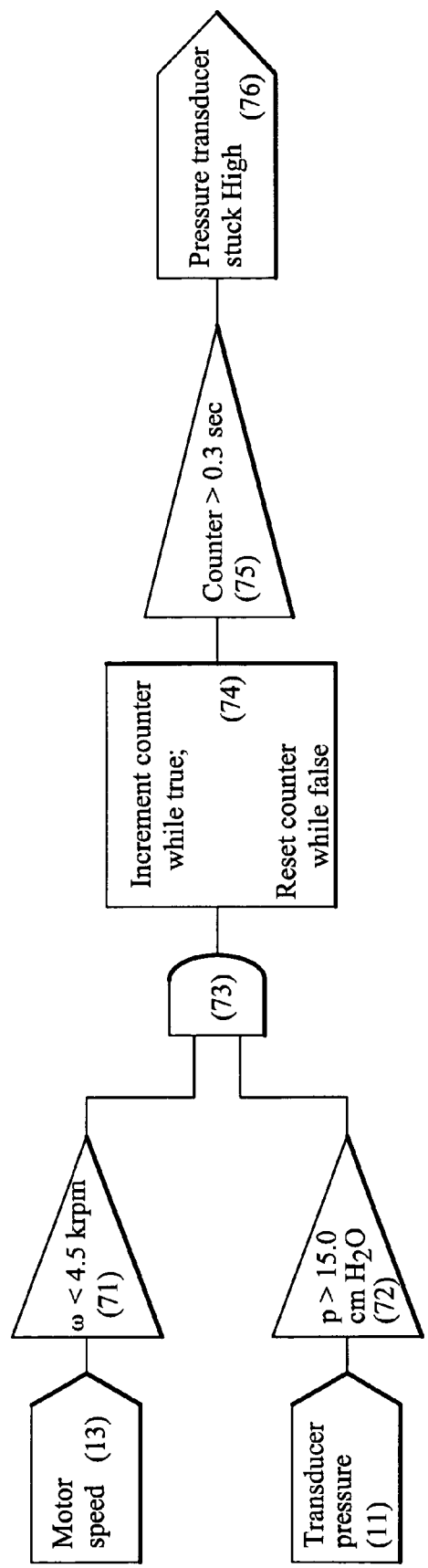
Figure 7: *Detect Pressure Transducer Stuck High*

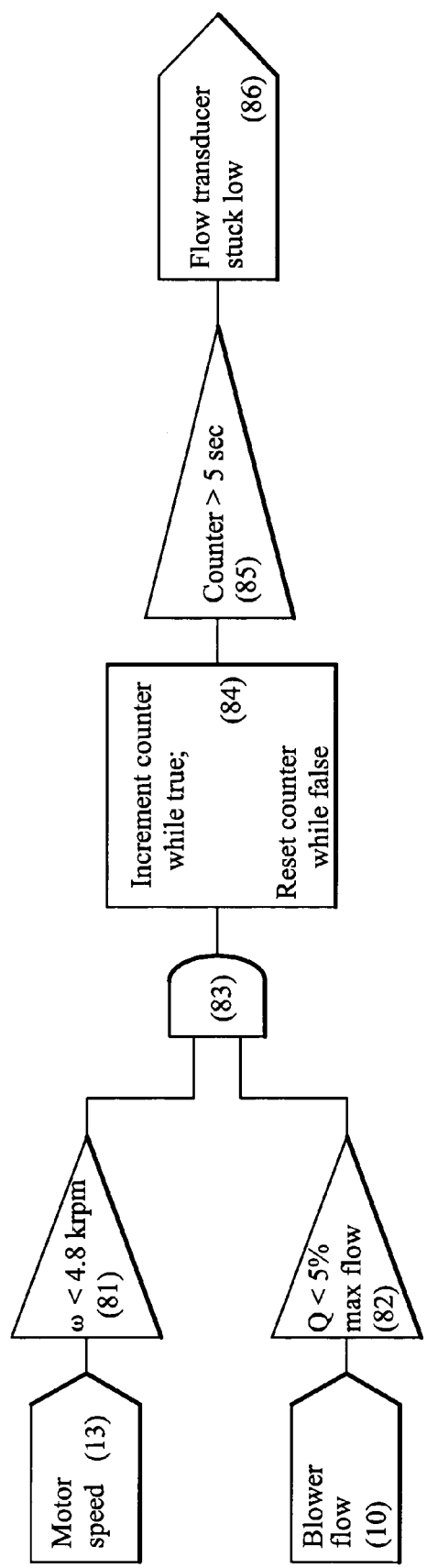
Figure 8: *Detect Flow Transducer Stuck Low*

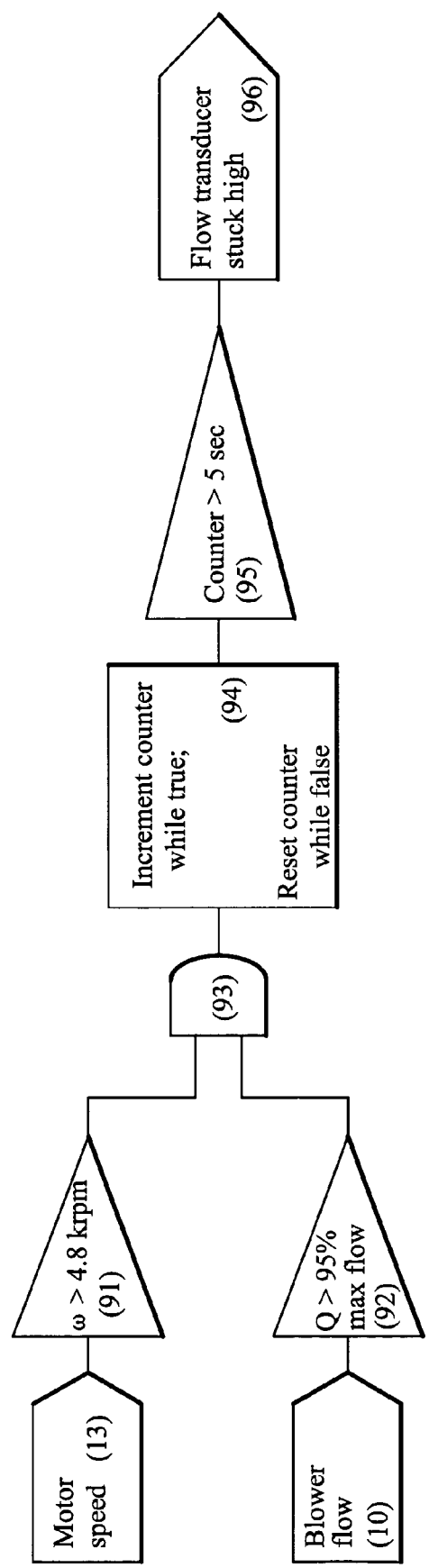
Figure 9: *Detect Flow Transducer Stuck High*

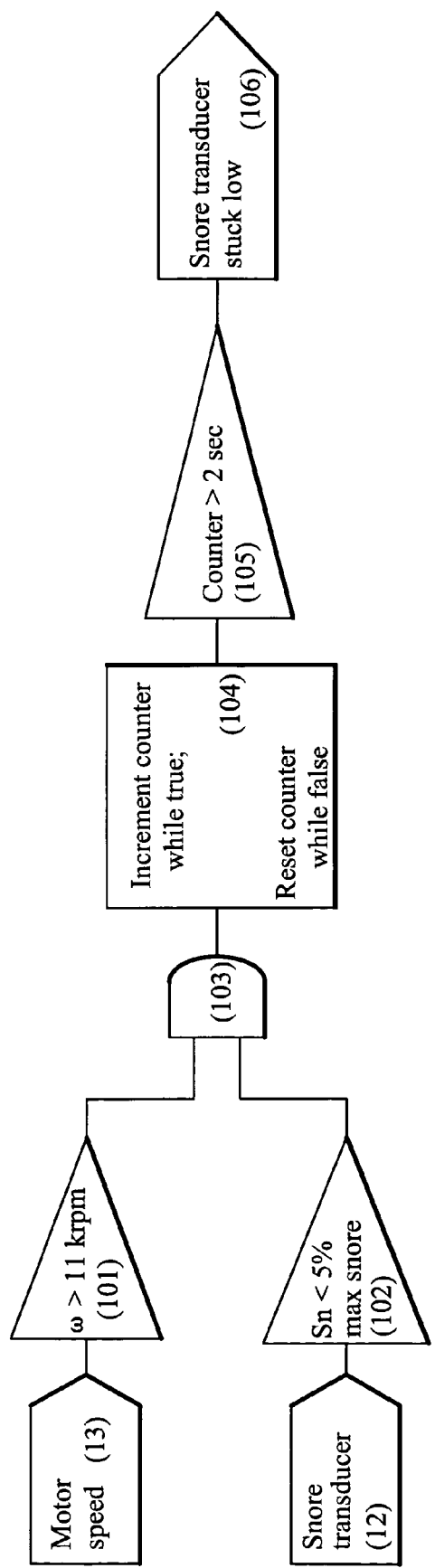
Figure 10: *Detect Snore Transducer Stuck Low*

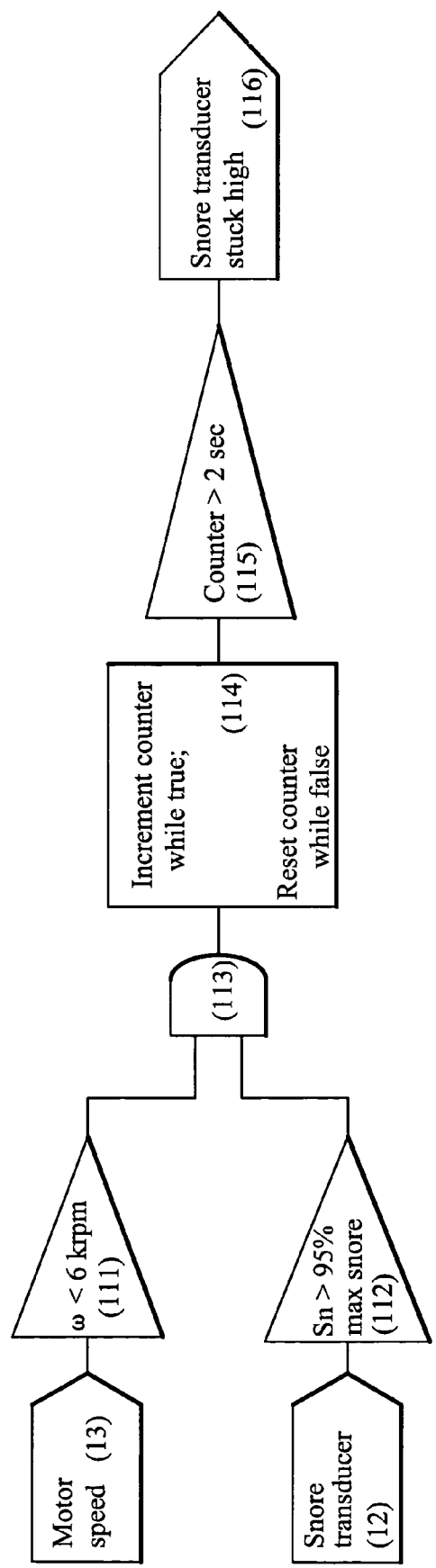
Figure 11: *Detect Snore Transducer Stuck High*

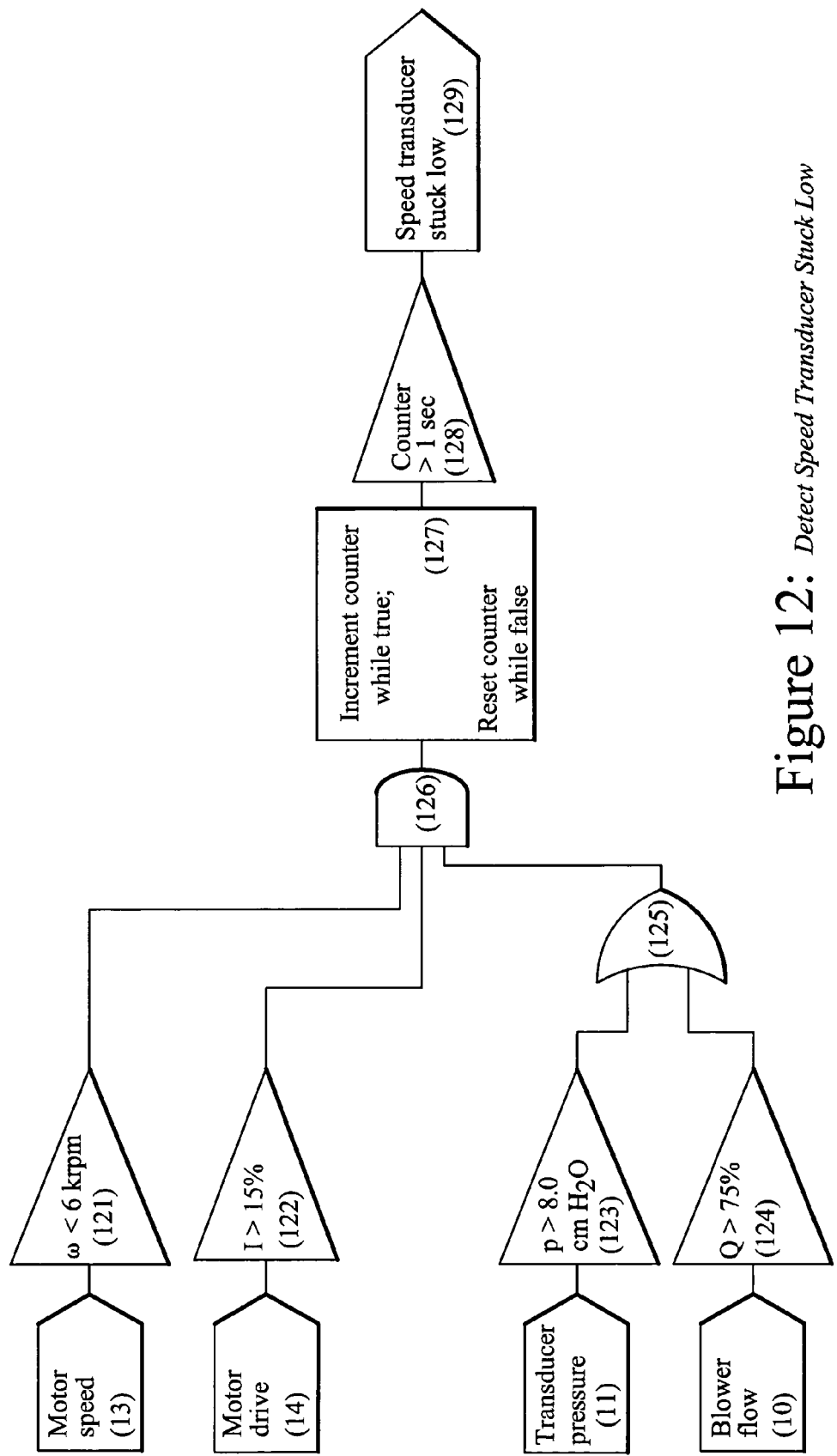
Figure 12: *Detect Speed Transducer Stuck Low*

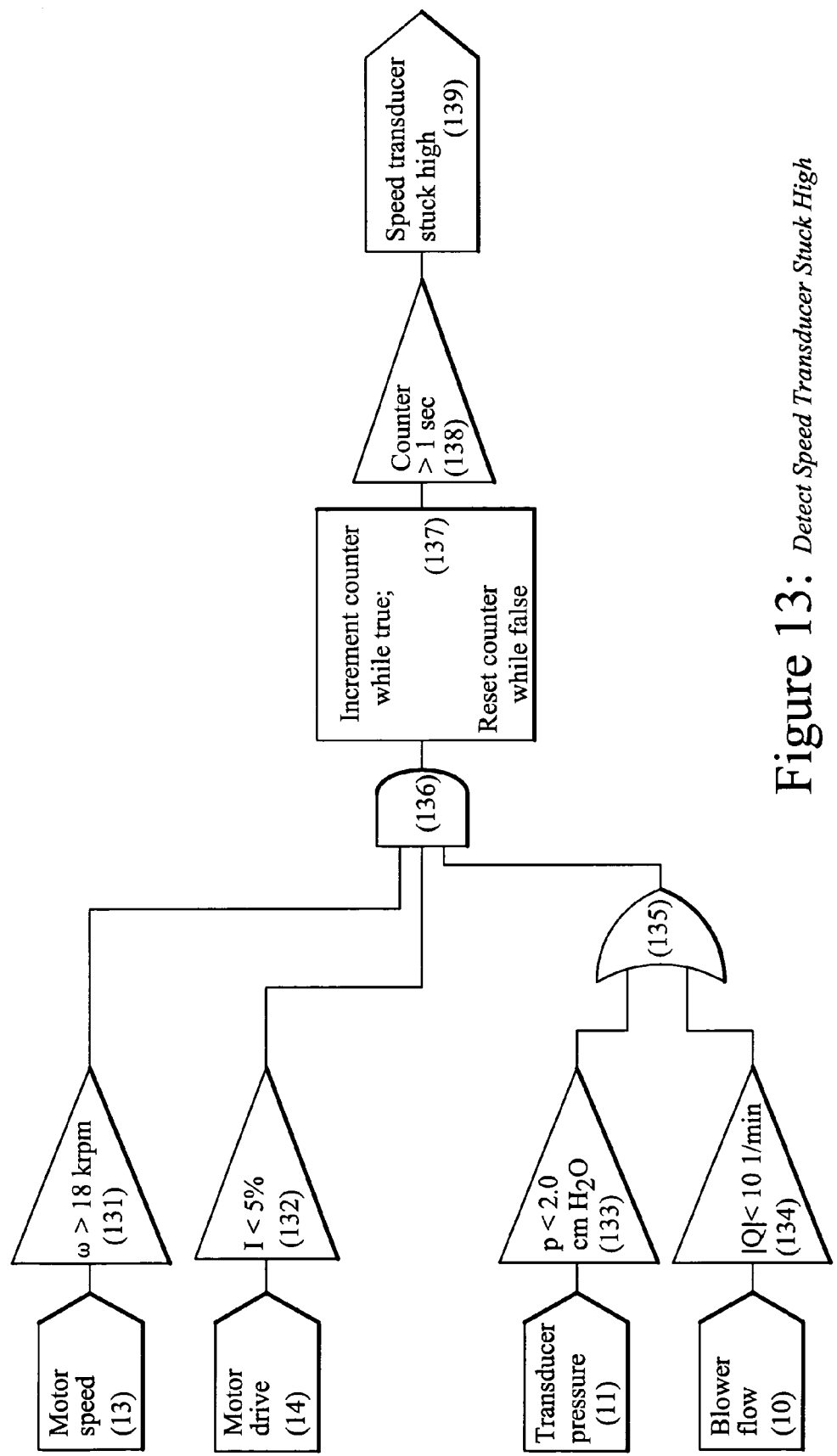
Figure 13: *Detect Speed Transducer Stuck High*

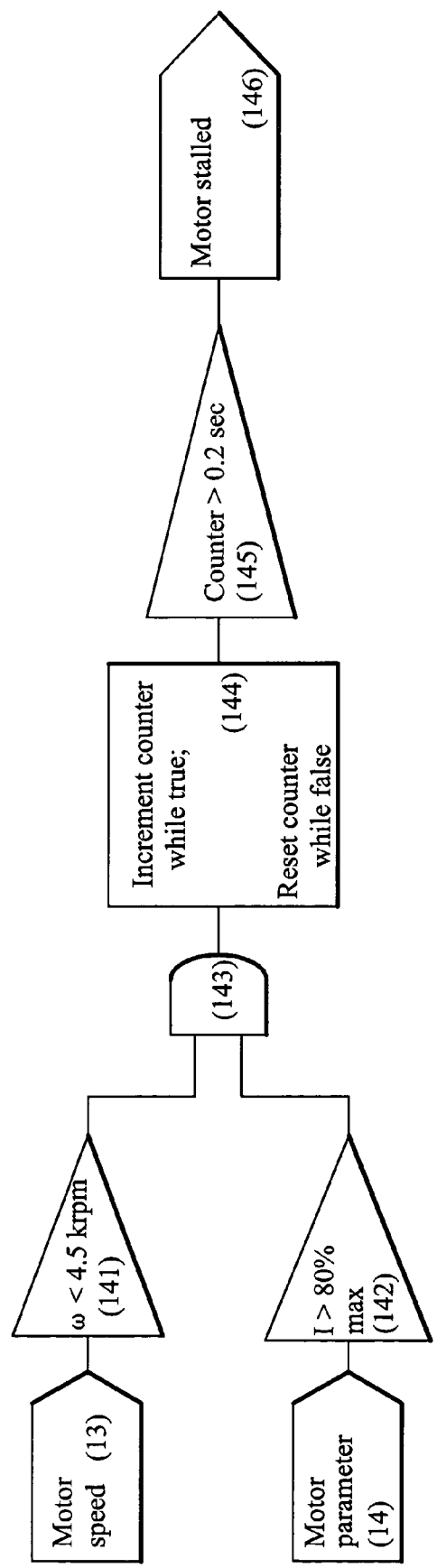
Figure 14: *Detect Stalled Motor*

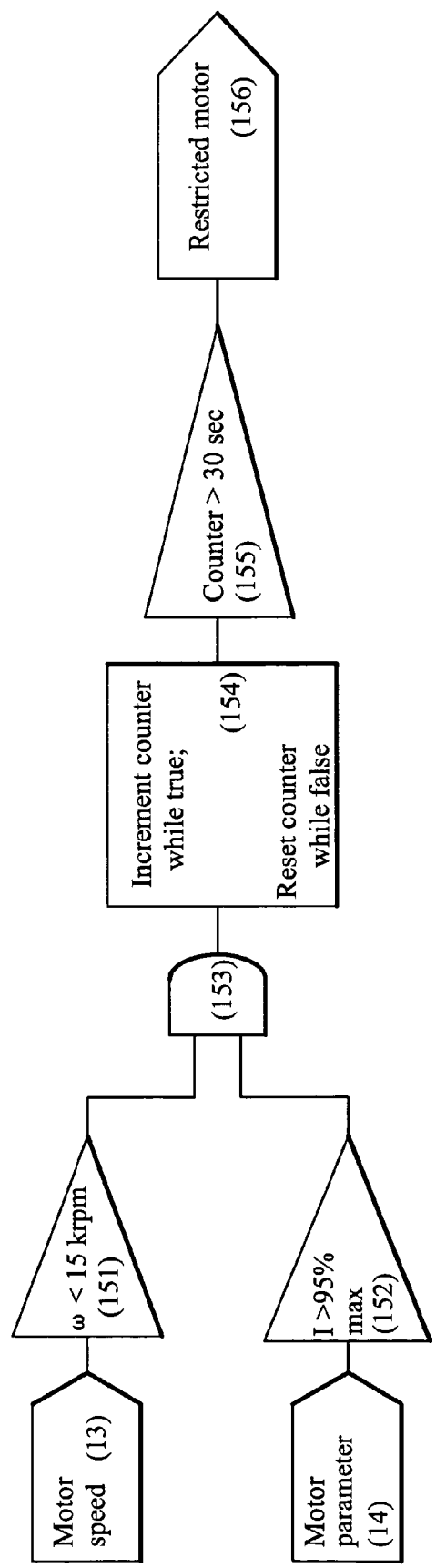
Figure 15: *Detect Restricted Motor*

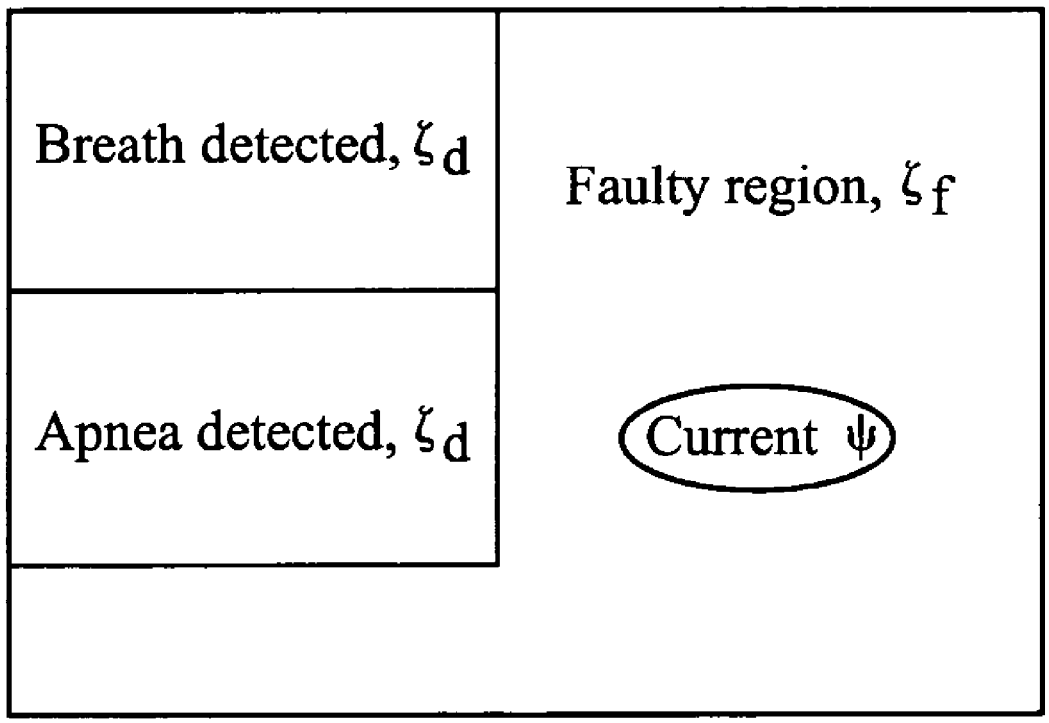
Figure 16: *Software fault*

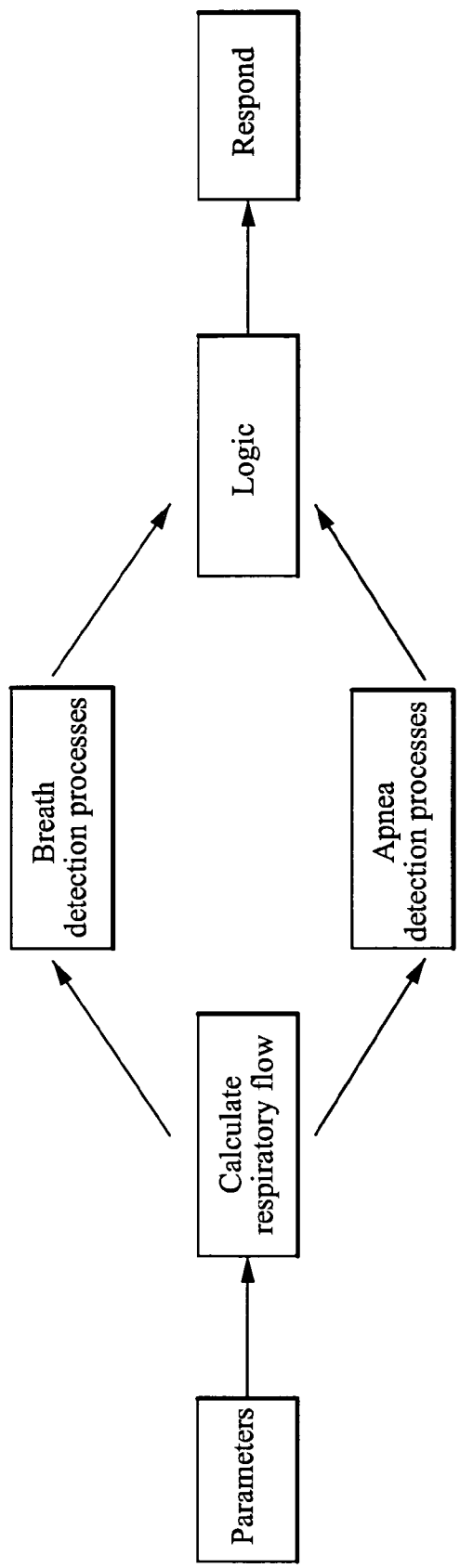
Figure 17: *Software fault detection processes*

FAULT DIAGNOSIS IN CPAP AND NIPPV DEVICES

This application is a divisional of U.S. application Ser. No. 10/408,568, filed Apr. 8, 2003, now U.S. Pat. No. 6,745,768, which is a continuation of U.S. application Ser. No. 09/719,680, filed Jun. 5, 2001, now U.S. Pat. No. 6,591,834, which is a National Phase of PCT/AU99/00972, filed Nov. 5, 1999 and claims priority of Australian Application No. PP 6933, filed Nov. 5, 1998, the contents of which are incorporated herein by reference in their entirety.

BACKGROUND OF THE INVENTION

This invention relates to ventilation devices such as non-invasive positive pressure ventilation (NIPPV) and continuous positive airway pressure (CPAP) devices which function to supply a patient with a supply of clean breathable gas (usually air, with or without supplemental oxygen) at a prescribed pressure or pressures at appropriate times during the patient's breathing cycle. The specification discloses a method and apparatus for fault diagnosis in such devices.

An example of a suitable device in which the invention may be included is the AutoSet® device (ResMed Ltd., Australia), which may be used for treating sleep disordered breathing, such as Obstructive Sleep Apnea (OSA), as described in U.S. Pat. No. 5,704,345 (Berthon-Jones).

A NIPPV or CPAP device typically includes a flow generator, an air filter, a mask, an air delivery conduit connecting the flow generator output to the mask, various sensors and a microprocessor-based controller. The flow generator may include a servo-controlled motor and an impeller. The sensors measure, among other things, motor speed, gas volumetric flow rate and pressure. The air delivery circuit is that portion of the device's airflow path comprising the air inlet, the filter, the flow generator, the conduit and the mask. The device may optionally include a humidifier in the air delivery circuit. The controller may include data storage means.

One problem compromising the effective operation of such devices is that with time, the air inlet filter may become dirty, increasing the filter's resistance to the flow of air. It is known to provide a warning light which is activated after a given number of hours of operation of the device, to indicate that the filter should be cleaned or replaced. Such an approach does not take into account the fact that the rate of accumulation of dirt on the filter will depend on the environment in which the device is used. It may also be found that the patient may continue to use the device despite the warning light and thereby receive inadequate therapy. Importantly, the air delivery circuit may become partly or completely blocked for other reasons, without a warning being given.

SUMMARY OF THE INVENTION

At a given rotational speed of the motor, and a given air delivery circuit pneumatic impedance, the flow generator will deliver gas at a particular pressure. By measuring the resultant pressure for a range of motor speeds, for different circuit impedances, and with and without the humidifier, characteristic curves of the device may be obtained. If then the values of motor speed, flow rate and pressure are measured by transducers during operation of the device, the current pneumatic impedance may be calculated from the appropriate characteristic curve. It is therefore possible to estimate the resistance of the air filter and thus more accurately indicate when the filter needs changing. Furthermore, partial or complete blockage of the air delivery circuit will also be capable of detection by such an arrangement.

An acceptable range of measured pressure values may be calculated for a given set of conditions, defined, for example, by upper and lower characteristic curves. The motor speed may be increased to maintain an acceptable output pressure as a response to increased impedance, while a pressure outside an acceptable range may be indicative of the need to replace the filter.

Such an arrangement relies on the transducers providing correct information regarding the monitored parameters, and in accordance with preferred forms of the invention the existence of transducer fault conditions is also responded to by the system.

The invention therefore broadly resides in a method or apparatus in which, in each case, acceptable and unacceptable regions for transducer values are chosen. During operation of the device, the transducer values are measured and compared with the predetermined regions. When the transducers are in unacceptable regions, corrective action is taken, for example, by issuing a warning of the fault or shutting down the device.

Thus, in one form, the present invention provides apparatus for supplying breathable gas to a patient, including a gas flow generator, a gas delivery circuit, a controller having data storage means, sensors monitoring values of operational parameters of the apparatus, and fault detection means including at least one relationship stored in said data storage means, said relationship relating a combination of values of at least two of said parameters as indicative of a fault condition of said apparatus, said fault detection means further including means testing said at least two said monitored operational parameter values against said stored relationships and instigating a response upon detection of a fault condition.

Preferably, said monitored parameters include at least motor speed of the flow generator, gas flow rate and gas delivery circuit pneumatic pressure.

In the practice of this aspect of the invention, a device embodying the invention will before clinical use be subjected to a calibration routine in which the motor speed and air delivery circuit pneumatic pressure are varied, while measuring pressure and flow rate. From these measurements characteristic curves are determined and stored in the data storage means associated with the controller.

During clinical use, flow rate, pressure and speed are monitored. The appropriate characteristic curves and acceptable range of pressure are selected for the current set of operating conditions. The measured pressure is tested against the acceptable range, and if it lies outside that range, a fault is asserted. If a fault is asserted, an error message may be given on the output screen, an alarm given, or the machine may be shut down.

In other embodiments of the invention, all of the transducers (such as snore, flow and speed transducers) are tested against predetermined characteristic curves for fault conditions.

Further embodiments are described below in relation to CPAP apparatus, but will be understood as being applicable to any of the above described forms of ventilatory treatment or assistance.

BRIEF DESCRIPTION OF THE DRAWINGS

FIGS. 1(a) to (d) illustrate possible configurations of a device employing a humidifier and a loop back box.

FIG. 2 CPAP Apparatus

FIG. 3 Desirable operating region for blower (a) high speed, and (b) low speed

FIG. 4 Computer software block diagram

FIG. 5 Pressure transducer fault regions

FIG. 6 Flowchart: Detect pressure transducer stuck low

FIG. 7 Flowchart: Detect pressure transducer stuck high

FIG. 8 Flowchart: Detect flow transducer stuck low

FIG. 9 Flowchart: Detect flow transducer stuck high

FIG. 10 Flowchart: Detect snore transducer stuck low

FIG. 11 Flowchart: Detect snore transducer stuck high

FIG. 12 Flowchart: Detect speed transducer stuck low

FIG. 13 Flowchart: Detect speed transducer stuck high

FIG. 14 Flowchart: Detect stalled motor

FIG. 15 Flowchart: Detect restricted motor

FIG. 16 Software fault diagnosis regions

FIG. 17 Flowchart: Software fault diagnosis

In the figures, the "D" symbol is a logical "and", the rectangle symbol is a block of code. The triangle symbol is a comparator, if the conditions are met, then the output is a logical "1", otherwise "0".

DETAILED DESCRIPTION OF THE PREFERRED EMBODIMENTS

An example of a problem solved by the present invention is provided by the Applicant's AutoSet® T device, which is provided with a "loop back" box which facilitates the optional connection of a humidifier into the air delivery circuit upstream of the pressure transducer. The arrangement is described in co-pending Australian patent application No. 71978/98 filed 18 Jun. 1998 and is schematically illustrated in FIGS. 1(a) to (d) hereof.

FIGS. 1(a) and (b) show the correct manner in which the loop back box and the humidifier are intended to be connected. In FIG. 1(a) the humidifier is not used, and the loop back box connects the flow generator (F) to the internal conduit where the pressure sensor (T) is located. The mask (M) is connected to its outlet downstream of the pressure sensor.

Typically the ventilatory assistance for CPAP or NIPPV treatment is delivered to the patient by way of nasal mask. Alternatively, a mouth mask, a full face mask or nasal prongs can be used. In this specification, any reference to a mask is to be understood as incorporating a reference to a nasal mask, mouth mask, full face mask or nasal prongs.

In FIG. 1(b) the humidifier (H) replaces the loop back box and gas correctly flows from the flow generator, through the humidifier, past the pressure transducer and thus to the mask.

In order that the AutoSet® device be compatible with a large range of standard tubing, humidifiers and masks, the outlets all have the same size and shape. It is therefore possible to assemble the equipment incorrectly, as shown in FIGS. 1(c) and (d). In FIG. 1(c) neither the loop back box nor the humidifier is used, and the mask is attached directly to the outlet of the flow generator, thus by-passing the pressure sensor. In FIG. 1(d) the mask receives no pressurised air. In either of these situations the pressure transducer will give an incorrect indication of mask pressure and this may lead to a dangerous overpressure in an automatically adjusting device.

By monitoring the pressure transducer output in conjunction with motor speed this dangerous condition can be detected and responded to. Boundary conditions of high motor speed and low pressure, and low motor speed and high pressure, may be chosen as indicators of a fault condition. The same conditions can also be used to assert a fault in the case of a defective pressure transducer, and are described later in relation to FIGS. 6 and 7.

A similar approach enables a stalled motor condition to be catered for in the NIPPV device without the use of devices such as fuses. A stalled motor will not generate any pressure, and the feedback control loop to the servo unit will cause an increase in motor current. Conventionally, a fuse or other cut-out device will be required to protect the motor from overheating. If however, the motor parameters of motor speed and a motor drive parameter such as a function derived from current are monitored, a fault condition may be established. For example, if the motor parameter is greater than 80% and the motor speed remains below 4,500 rpm for 0.2 seconds, a "Stalled Motor" condition exists. A "Restricted Motor" condition can also be defined, for example where the motor parameter exceeds 95% and the motor speed is lower than 15,000 rpm, for at least 30 seconds.

The corrective action in these cases is to disable the motor and otherwise disable operation of the machine until service can be performed, this mode being termed the "service required" mode.

Malfunction of the motor speed transducer will impact on the detection of motor stall, and on other fault detection functions which will be described below. In this specification there is therefore also described the manner in which the invention may be applied to the detection of motor speed transducer failure.

It will be seen that the invention can be put into effect with appropriate software, using the control electronics already provided in the machine, and therefore represents an economical solution to the diagnostic objectives.

Advantages of the Invention

The invention has a number of advantages over the prior art. Firstly, safety can be improved. The greatest proportion of CPAP treatment apparatus are for use in a non-clinical setting, in which environment a user is untrained to detect conditions indicative of faults. Such fault conditions can lead to the CPAP treatment apparatus being ineffective or even dangerous. For example, the flow generators used in certain modem CPAP treatment apparatus are capable of delivering pressures in excess of 30 cm $H_2O$, which may be required in certain situations, but excessive and potentially dangerous in others.

The costs, both direct and associated, of CPAP treatment apparatus which include the invention can be reduced. Certain hardware such as fuses and other analogue circuitry may no longer be required. Furthermore, it becomes cheaper for technicians to diagnose faults since the device may be interrogated by interfacing with the controller, reducing the need to remove casing during service. Interfacing may be done locally or remotely, for example through a network. In a clinical setting, this may have the further advantage of reducing patient disturbance.

In the CPAP treatment device with fault diagnosis, useability is improved. It becomes possible to provide fault diagnosis and rectification information to those without clinical or technical skills.

The invention may also be used to predict more accurately when faults may occur, for example, to predict when a flow generator air inlet filter may need changing, based on measurements of the motor load.

In the specification, any reference to "operating parameters" is to be understood to relate to any form of data or state signal, transducer or actuator, and the mechanical and electrical functions of component elements/apparatus of a CPAP apparatus. Any reference to "process" is to be understood to mean a unit of hardware and/or software which can perform a task or set of related tasks, for example, a fault detection process, a feedback control process, a pressure measurement process or a flow measurement process.

Following the diagnosis of a current or potential fault occurring, the response may be one or more of the following: issuing a warning of the fault condition, recording a diary entry describing the fault condition, adjusting operating parameters and switching between the functional and stand-by or stop modes, or switching the device to a service-required mode. The response may be immediate, or at some later period, for example, the morning following the sleep period during which the device was used.

FIG. 2 shows a simplified schematic of a typical CPAP treatment apparatus. An impeller (1) is powered by an electric motor (2) using a servo (3) under the direction of a microprocessor-based controller (4). The supply of breathable gas is carried to the mask (5) through a flexible conduit (6). The apparatus has various switches (7), displays (8) and a number of transducers. The transducers monitor a number of processes, for example: volumetric flow rate (10) (at a predetermined point in the flow path), pressure (11) (at a predetermined point downstream of the flow generator outlet or at the mask), snore (12), flow generator rotational speed (13) and motor parameter (14).

The Concept of an Acceptable Region: Hardware Operation

There may be a relationship between the measured blower flow rate, f, and the measured blower output pressure, p, such that f decreases when p increases. It may be desired that for acceptable operation of the device, the parameter values be kept in a certain region. The function R for that process may be written:

$$R = R(f, p)$$

Distinct functions may be determined for different conditions, for example, high and low motor speeds, as shown in FIGS. 3a and 3b. Alternately, the acceptable region could be defined by a 3-parameter model, $R = R(f, p, \omega)$, where $\omega$ is motor speed.

Example of a Logical Test

In a simple case, the acceptable region may be a rectangle, defined by two values of flow $f_1$ and $f_2$ and two values of pressure, $p_1$ and $p_2$. If the estimates of the parameter values were $\{f, p\}$ then the test to diagnose a current fault may be, for example:

If $p > p_1$ and $p < p_2$ and $f > f_1$ and $f < f_2$ then the current operation region lies within the acceptable range.

Alternatively, the method may diagnose a fault if $\{f, p\}$ lay outside the acceptable range for an instant, or lay outside the desirable range for some duration.

Computer Software Block Diagram

Advantageously, the invention is implemented in software. In this case, no additional hardware is needed. The fault detection software processes may be executed in conjunction with existing software. This is shown in FIG. 4. The inputs to the controller (4) are analogue electronic signals indicative of the value of various sensors, transducers and other electronic circuitry. These are converted to digital signals. The hardware parameter values (41) are passed to one or both of the normal computer software processes (44) (for example, feedback control processes) and the fault diagnosis processes (43). Further parameters may be generated (42) (for example, flags) indicative of the operation of each of the software processes, and passed back into one or both of the software processes. In addition, the processes may generate hardware instructions (45) (for example, information to be displayed, or directions to shut down the operation of the CPAP device) which are converted to analogue electronic signals and passed to the relevant hardware.

Fault diagnosis of each apparatus process may be executed as a distinct software process, or several apparatus processes may be monitored within a single software process.

Preferred Mode of Operation

Processes Monitored

In the preferred mode of carrying out the invention, in each device, a plurality of processes are monitored. These include:

Pressure transducer operation
Flow transducer operation
Snore transducer operation
Speed transducer operation
Motor operation
Breath and Apnea detection algorithms
Fault diagnosis process operation
Air filter operation
Correct assembly of air delivery circuit Modes of fault diagnosis for these processes are described in the following sections.

Pressure Transducer

The invention may be used to detect whether the pressure transducers are correctly operating. A consequence of a failure of a pressure transducer (11) could be overpressure or under-pressure to the mask and thus the patient. To detect such a failure condition, the transducer pressure is monitored (11) together with motor speed (13). The regions of faulty device operation are shown in FIG. 5. Logical flow-charts indicating the decision process are shown in FIGS. 6 and 7.

If the sensed pressure remains below 2.0 cm $H_2O$ (62) while the motor speed is above 12,000 rpm (61) for at least 0.3 seconds (65), a fault condition is signalled as a "Pressure Transducer Low" failure (66). If neither condition is satisfied, a timer is reset (64).

In a similar way, if the pressure value remains above 15 cm $H_2O$ (72) while the motor speed is below 4,500 rpm (71) for at least 0.3 seconds (75), that corresponds to a "Pressure Transducer High" failure (76). On detection of either form of pressure transducer failure, corrective action is taken to disable power to the motor (2) and a notification is given on a display. The user may then check all components in the air delivery circuit for an obstruction or an incorrect connection.

An additional embodiment is used for the pressure transducer fault diagnosis mode in conjunction with motor speed. The output from the pressure transducer is split into two signals. One signal, $P_{high}$ remains unfiltered, whilst the other signal is low-pass filtered to become $P_{low}$. Each signal is tested to yield an output of "Pressure Transducer High", "Pressure Transducer Low" or "ok". The conditions for "high" and "low" are as described above. A signal which is neither high nor low is deemed to be ok. Unless the test result for both signals is "ok", a fault condition will be signalled. If the test result for both signals is "low", the fault condition is taken as an indication that the hoses are not connected.

Flow Transducer

A failure of the flow transducer (10) can cause errors in flow measurement, mask pressure measurement and signal processing (such as inspiratory flow flattening index, as taught in U.S. Pat. No. 5,704,345). This in turn may result in errors in the delivery pressure from the flow generator (1), compromising the efficacy of treatment. Logical flowcharts indicating the decision process are shown in FIGS. 8 and 9.

To detect such a fault, the flow transducer (10) signal is monitored together with motor speed (13). If the flow remains below 5% full scale deflection (f.s.d.)(82) while the motor speed is less than 4,800 rpm (81) for more than five seconds (85), the fault condition is signalled as "Flow Transducer Low" failure (86). If neither condition is satisfied the counter is reset (84). In a similar manner, if the flow generator flow remains above 95% f.s.d. (92) with the motor speed less than 4,800 rpm (91) for more than 5.0 seconds (95), the fault of "Flow Transducer High" is signalled (96).

On occurrence of either fault condition, the patient is notified on a display, and in addition, the mask pressure will be increased over some time, for example, five minutes, to a predetermined level, in this case, the 95% centile of the previous session. However if that pressure value would be invalid by representing a dangerous overpressure, the pressure will be limited to 10 cm $H_2O$.

Snore Transducer

A failure of the snore index transducer can cause errors in the snore measurement and the calculated snore index. Such errors result in consequential errors in the treatment pressure delivered by the flow generator (1), again possibly compromising the efficacy of treatment. Logical flowcharts indicating the decision process are shown in FIGS. 10 and 11.

To detect a failed snore transducer the snore transducer signal (12) and motor speed (13) are sampled. If the snore index signal remains below 5% f.s.d. (102) with the motor speed greater than 11,000 rpm (101) for more than two seconds (105), a "Snore Transducer Low" failure is signalled (106). If neither condition is satisfied the counter is reset (104). If the snore transducer (12) signal remains above 95% f.s.d. (112) while the motor speed is less than 6,000 rpm (111) for more than two seconds (115) a "Snore Transducer High" failure mode occurs (116).

The corrective action that can be taken is to notify the user of the occurrence and, if the flow generator (1) is generating a pressure, attempt to increase the pressure over some time, for example 5 minutes, to a predetermined level, for example, the 95% centile of the previous session. If that pressure value is invalid by representing a dangerous overpressure, the pressure will be limited to 10 cm $H_2O$.

Motor Speed Transducer

An incorrect motor speed may impact upon functions arising from the pressure transducer (11), flow transducer (10) and snore transducer (12). Logical flowcharts indicating the decision process are shown in FIGS. 12 and 13. Detection of a failure of the motor speed transducer (13) is achieved by monitoring the speed (13) together with the sensed pressure (11) and flow (10) and the motor drive parameter (14). If the motor speed remains below 6,000 rpm (121) while the motor drive parameter is above 15% (122) and either the pressure is above 8.0 cm $H_2O$ (123) or (125) the flow is greater than 75% f.s.d. (124), this set of conditions being true for more than one second (128), then a "Motor Speed Low" failure is signalled as occurring (129). If any of the conditions are not met, the counter is reset (127).

If the motor speed remains above 18,000 rpm (131) while the motor drive is below 5% (132) and (136) either the pressure is below 2.0 cm $H_2O$ (133) or (135) the absolute flow is less than 10 l/min (134) for more than one second (138), a "Motor Speed High" failure is signalled as occurring (139).

The corrective action that can be taken is to notify the user of the occurrence and, if the flow generator (1) is generating a pressure, attempt to increase the pressure over some time, for example 5 minutes, to a predetermined level, for example, the 95% centile of the previous session. If that pressure value is invalid by representing a dangerous overpressure, the pressure will be limited to 10 cm $H_2O$.

Motor

As noted earlier, a stalled motor will not generate any pressure. Such a condition can occur if the impeller (1) is jammed, for example. The feedback control loop from the flow generator (1) to the servo unit (3) will cause an increase in the power delivered to the motor (2), the increase continuing until maximum power is supplied. A consequence can be overheating of the motor to the extent that insulation or windings fail and the motor must be replaced. Flowcharts describing the operation for "stalled" and "restricted" motor are shown in FIGS. 14 and 15 respectively.

A motor failure condition is detected by monitoring the motor speed (13) and motor drive parameter. If the motor parameter is greater than 80% (142) and (143) the motor speed remains below 4,500 rpm (141) for 0.2 seconds (145), a "Stalled Motor" condition exists (146). If any of the conditions are not met, the timer is reset (144). In a similar way, if the motor parameter exceeds 95% (152) and the motor speed is lower than 15,000 rpm (151), occurring for more than 30 seconds (155), then a "Restricted Motor" condition exists (156).

The corrective action is to disable power to the motor and otherwise disable operation of the machine until a service can be performed, this mode being termed the "service-required" mode.

Pneumatic Performance

In another embodiment, the method may be used to check the overall pneumatic, or air delivery, performance of the apparatus. The relevant regions are shown in FIG. 3, being the desired operating region $\zeta_d$ and fault regions $\zeta_{f1}$, $\zeta_{f2}$. The operating regions are a function of pressure (p), flow (f) and motor speed ($\omega$). If, the operational state of the device lies in region $\zeta_{f1}$, there are several possible causes:

Dirty filter
Internal air path blockage in the CPAP apparatus
Leak in the internal air path of the CPAP apparatus
Flow generator failure
Faulty speed sensor
Faulty flow sensor
Faulty pressure sensor Possible responses include:

Issuing a warning advising that the filter needs changing
Switching the apparatus to service-required mode If the operational state of the device lies in region $\zeta_{f2}$, there are several possible causes:

Faulty speed sensor
Faulty flow sensor
Faulty pressure sensor

The response would be to switch the device to the service required mode.

The embodiments described earlier may be used in conjunction with the current embodiment, to distinguish which of the sensors may be faulty.

Fault Diagnosis Operation

The events "pressure transducer stuck high" and "pressure transducer stuck low" are mutually exclusive. Similarly the flow, snore and motor speed transducers have mutually exclusive conditions. In another embodiment of the invention, the fault diagnosis processes tests whether mutually exclusive conditions have been deduced and signals an error in fault diagnosis if that event occurs.

Breath and Apnea Detection Processes

FIG. 16 shows the operating regions for the breath and apnea detection processes. These processes detect the presence of breathing by the user and the occurrence of apneas, these two events being mutually exclusive. During normal operation of the CPAP device, either one or the other of these events ought to be detected. In this case, these two events lie within non-intersecting regions of $\zeta_d$ (FIG. 16). If the current operating region of the device lies outside both these two regions, then some kind of error has occurred and an error is asserted. A flowchart for this fault detection process is shown in FIG. 17. While the device is operating the "Breath Detection" and "Apnea Detection" processes are monitored. The fault detection process will assert a fault when either of the following two conditions occur:

Apnea and Breath are asserted simultaneously

Neither Apnea nor Breath are asserted for a predetermined period.

While particular embodiments of this invention have been described, it will be evident to those skilled in the art that the present invention may be embodied in other specific forms without departing from the essential characteristics thereof. The present embodiments and examples are therefore to be considered in all respects as illustrative and not restrictive, the scope of the invention being indicated by the appended claims rather than the foregoing description, and all changes which come within the meaning and range of equivalency of the claims are therefore intended to be embraced therein.

The invention claimed is:

1. A method of detecting a fault in an apparatus for supplying breathable gas to a patient at a positive pressure, the apparatus including a gas flow generator comprising a servo controlled motor and impeller, a motor speed transducer configured to monitor motor speed, a snore transducer configured to produce a snore transducer signal, and a timer, the method comprising:

monitoring the motor speed;

monitoring the snore transducer signal;

following a predetermined duration, comparing the snore transducer signal to a first threshold and the motor speed to a second threshold to derive a first compared value and a second compared value, respectively; and determining a snore transducer fault in accordance with the first compared value and the second compared value.

2. The method of claim 1, further comprising determining that the snore transducer is stuck low if the first compared value indicates that the snore transducer signal is below the first threshold and if the second compared value indicates that the motor speed is above the second threshold.

3. The method of claim 2, wherein the first threshold is below 5% full scale deflection.

4. The method of claim 2, wherein the second threshold is greater than 11,000 RPM.

5. The method of claim 1, wherein the predetermined duration is more than 2 s while the motor speed is less than 6,000 RPM.

6. The method of claim 1, further comprising determining that the snore transducer is stuck high if the first compared value indicates that the gas flow is above the first threshold and if the second compared value indicates that the motor speed is below the second threshold.

7. The method of claim 6, wherein the first threshold is above 95% full scale deflection.

8. The method of claim 6, wherein the second threshold is less than 6,000 RPM.

9. A method of operating an apparatus for supplying breathable gas to a patient at a positive pressure, the apparatus including a gas flow generator comprising a servo controlled motor and impeller, a motor speed transducer, a snore transducer configured to produce a snore transducer signal, and a display, the method comprising:

determining a snore transducer fault;

providing a warning notice on the display; and if the flow generator is generating a pressure, changing mask pressure over a predetermined period of time.

10. The method of claim 9, wherein the pressure is increased and the predetermined period of time is approximately 5 minutes.

11. An apparatus for supplying breathable gas to a patient at a positive pressure, including a gas flow generator comprising:

a servo controlled motor and impeller;

a motor speed transducer configured to monitor motor speed;

a snore transducer configured to produce a snore transducer signal;

a timer; and a controller configured to:

monitor the motor speed transducer, the snore transducer, and the timer;

compare, following a predetermined duration, the snore transducer signal to a first threshold and the motor speed to a second threshold to derive a first compared value and a second compared value, respectively; and determine a snore transducer fault in accordance with the first compared value and the second compared value.

12. The apparatus of claim 11, wherein the controller is further configured to determine that the snore transducer is stuck low if the first compared value indicates that the snore transducer signal is below the first threshold and if the second compared value indicates that the motor speed is above the second threshold.

13. The apparatus of claim 12, wherein the first threshold is below 5% full scale deflection.

14. The apparatus of claim 12, wherein the second threshold is greater than 11,000 RPM.

15. The apparatus of claim 11, wherein the predetermined duration is more than 2 s while the motor speed is less than 6,000 RPM.

16. The apparatus of claim 11, wherein the controller is further configured to determine that the snore transducer is stuck high if the first compared value indicates that the snore transducer signal is above the first threshold and if the second compared value indicates that the motor speed is below the second threshold.

17. The apparatus of claim 16, wherein the first threshold is above 95% full scale deflection.

18. The apparatus of claim 16, wherein the second threshold is less than 6,000 RPM.

19. An apparatus for supplying breathable gas to a patient at a positive pressure, including a gas flow generator comprising:
- a servo controlled motor and impeller;
- a motor speed transducer;
- a snore transducer configured to provide a snore transducer signal;
- a display; and
- a controller configured to:
  - determine a snore transducer fault;
  - provide a warning notice on the display; and
  - if the flow generator is generating a pressure, change mask pressure over a predetermined period of time.

20. The apparatus of claim 19, wherein the mask pressure is increased and the predetermined period of time is approximately 5 minutes.

21. The apparatus of claim 20, wherein the mask pressure is increased to $95^{th}$ percentile pressure of a previous session.

22. The apparatus of claim 21, wherein the mask pressure is limited to 10 cm $H_2O$ if the $95^{th}$ percentile pressure is invalid.

* * * * *